United States Patent
Sakurai et al.

(10) Patent No.: US 8,362,400 B2
(45) Date of Patent: Jan. 29, 2013

(54) CERAMIC JUNCTION MEMBER, CERAMIC HEATER AND GAS SENSOR

(75) Inventors: Kikuo Sakurai, Ogaki (JP); Tomohiro Kuwayama, Kasugai (JP)

(73) Assignee: NGK Spark Plug Co., Ltd., Aichi (JP)

( * ) Notice: Subject to any disclaimer, the term of this patent is extended or adjusted under 35 U.S.C. 154(b) by 629 days.

(21) Appl. No.: 12/604,480

(22) Filed: Oct. 23, 2009

(65) Prior Publication Data

US 2010/0101950 A1  Apr. 29, 2010

(30) Foreign Application Priority Data

Oct. 24, 2008 (JP) ................................. 2008-274372
Sep. 30, 2009 (JP) ................................. 2009-225794

(51) Int. Cl.
*B60L 1/02* (2006.01)
(52) U.S. Cl. ......... 219/205; 219/202; 219/262; 219/267
(58) Field of Classification Search .................. 219/205, 219/202, 262, 267
See application file for complete search history.

(56) References Cited

U.S. PATENT DOCUMENTS

| 4,695,517 A | 9/1987 | Okuno et al. |
| 4,800,137 A | 1/1989 | Okuno et al. |
| 8,058,592 B2 * | 11/2011 | Kimata et al. ................ 219/538 |
| 2006/0283849 A1 * | 12/2006 | Sakurai et al. ............. 219/444.1 |

FOREIGN PATENT DOCUMENTS

| JP | 61-281089 A | 12/1986 |
| JP | 2007-022908 A | 2/2007 |

* cited by examiner

*Primary Examiner* — Kenneth Parker
*Assistant Examiner* — Dale E Page
(74) *Attorney, Agent, or Firm* — Sughrue Mion, PLLC (57) ABSTRACT

A ceramic joining unit, ceramic heater and gas sensor, the ceramic joining unit including: a ceramic base member; an electrode pad provided on a surface of the ceramic base member; a coupling terminal; and a joining portion, wherein the electrode pad includes: a first layer in contact with the ceramic base member; and a second layer laminated on a surface of the first layer and in contact with the joining portion, wherein each of the first and second layers contains a ceramic material as a main component, a content of the ceramic material in the first layer is greater than that of the second layer, and a contour of the first layer is located outside of a contour of the second layer at an entire periphery of the first layer.

8 Claims, 11 Drawing Sheets

CERAMIC JUNCTION MEMBER, CERAMIC HEATER AND GAS SENSOR

BACKGROUND OF THE INVENTION

1. Field of the Invention

The present invention relates to a ceramic junction member, a ceramic heater and a gas sensor.

2. Description of the Related Art

Conventionally, in a gas sensor employing a solid electrolytic member such as an oxide sensor, a ceramic heater is disposed in the gas sensor so as to heat the solid electrolytic member. A widely employed ceramic heater has been a type in which a heating resistor formed of a metal such as tungsten or molybdenum is embedded within a ceramic base member such as alumina. Further, an electrode pad electrically connected to the heating resistor is provided on the outer surface of the ceramic base member. A metallic coupling terminal for applying an external voltage to the heating resistor is soldered to the electrode pad.

In order to join different kinds of materials such as the ceramic base member, the electrode pad and the solder material, a technique has also been proposed which employs an electrode pad having two layers, namely, a first layer and a second layer (see Patent Document 1). The first layer contains a relatively large amount of ceramic material which is the main component of the ceramic base member and the second layer contains a relatively small amount of the ceramic material and in which the component of the soldering material for joining the electrode pad with the coupling terminal is sintered.

[Patent Document]

[Patent Document 1] JP-A-2007-22908

3. Problems to be Solved by the Invention

In the case of forming the second layer on the first layer, the second layer may be shifted from the first layer when the size of the first layer is substantially same as that of the second layer (that is, when the second layer is formed so as to deviate from the contour of the first layer). In this case, the misaligned portion of the second layer is not provided on the first layer but directly on the ceramic base member. Thus, adhesion of the second layer with respect to the ceramic base member as compared with that of the first layer is degraded. This is because the second layer is specified so as to adhere to the first layer and the soldering material, such that the misaligned portion of the second layer may exfoliate from the ceramic base member. Further, the entirety of the second layer may exfoliate starting at the misaligned portion of the second layer. That is, the coupling terminal may become separated from the ceramic base member.

SUMMARY OF THE INVENTION

The present invention has been made in view of the aforesaid problems, and an object thereof is to provide a structure which can suppress separation between a ceramic base member and a coupling terminal.

According to a first aspect (1), the present invention provides a ceramic joining unit comprising: a ceramic base member having a leading end side and a rear end side, said ceramic base member extending in a longitudinal direction; an electrode pad formed of at least one of tungsten and molybdenum, as a main component thereof, provided on a surface of the ceramic base member; a coupling terminal for electrical connection to an external circuit; and a joining portion which joins the electrode pad to the coupling terminal by means of a solder joint, wherein the electrode pad includes: a first layer in contact with the ceramic base member; and a second layer laminated on a surface of the first layer and in contact with the joining portion, wherein each of the first layer and the second layer contains a ceramic material as a main component among ceramic materials forming the ceramic base member, a content (wt %) of the ceramic material in the first layer is greater than a content (wt %) of the ceramic material in the second layer, and a contour of the first layer is located outside of a contour of the second layer at an entire periphery of the first layer.

According to this configuration, since the second layer is provided such that the contour of the first layer is located, at the entire periphery thereof, outside of the contour of the second layer, the second layer does not extend beyond the contour of the first layer. Thus, this arrangement prevents the second layer from being disposed directly on the ceramic base member. Consequently, the entire edge of the second layer can be firmly joined with the first layer so as to prevent exfoliation of the second layer.

In order to provide the second layer on the first layer so that the contour of the first layer is located outside of the contour of the second layer, the area of the second layer is set so as to be smaller than that of the first layer when viewed in the lamination direction of the electrode pad. That is, the first and second layers are viewed in the lamination direction of the electrode pad at the time of confirming the positional relation of these contours. Concretely, each of the contours is observed in the lamination direction of the electrode pad at the contour thereof.

The term "main component" as used herein means a material which content is 50 wt % or more among materials contained in a constituent element. That is, "an electrode pad which is formed of at least one of tungsten and molybdenum, as a main component thereof," means that the total content of tungsten and molybdenum (or the content of one of these materials when the other is not present) of all of the materials contained in the electrode pad is 50 wt % or more.

In a preferred embodiment (2) of the ceramic joining unit (1), the first layer is thicker than the second layer.

The second layer is joined with the soldering material formed of a metal as a main component thereof and the first layer formed of a metal as a main component thereof, while the first layer is joined with the ceramic base member formed of a ceramic material. As a result, adhesion between the ceramic base member and the first layer formed of materials comprising different main components is most degraded as compared with the remaining joining portions. Further, since the first layer is subjected to stress applied from both the second layer and the joining portion, the first layer is subjected to greater stress than the second layer which is only subjected to stress applied from the joining portion. In this respect, when the first layer is set to have a thickness greater than that of the second layer, the adhesion between the first layer and the ceramic base member can be sufficiently maintained. The first layer preferably has a thickness of 20 μm or more. On the other hand, when the second layer is set to have a thickness smaller than that of the first layer, the stress applied to the second layer can be reduced, whereby the adhesion between the second layer and the first layer can be further improved. Also, adhesion between the second layer and the joining portion can be further improved.

In another preferred embodiment (3) of the ceramic joining unit (1), the joining portion extends to a surface of the first layer over the second layer.

According to this configuration, since the joining portion extends to the first layer, the joining portion can be firmly joined with the electrode pad (including the first and second layers), so that separation of the coupling terminal from the ceramic base member can be further restrained.

Further, the joining portion is preferably provided so as to cover the second layer. In this case, since the second layer is not exposed, any external impact is not directly applied to the second layer. Thus, the second layer is less susceptible to separation from the first layer.

In yet another preferred embodiment (4) of the ceramic joining unit (3), a volume of the joining portion formed on the surface of the first layer is smaller than a volume of the joining portion formed on a surface of the second layer.

In order to improve adhesion with the ceramic base member, the first layer contains more ceramic material than the second layer. In contrast, when the joining portion extends to the first layer over the second layer, the electrode pad (including the first and second layers) can be firmly joined with the joining portion. However, since the ceramic material contained in the first layer migrates into the joining portion, adhesion between the ceramic base member and the first layer may degrade. Thus, when configured as in (4) above, migration of ceramic material into the joining portion from the first layer can be suppressed, and adhesion between the ceramic base member and the first layer can be maintained. On the other hand, when the joining portion having a greater volume is provided on the surface of the second layer which contains a ceramic material in an amount less than that contained in the first layer, adhesion between the electrode pad and the joining portion can be improved.

"A volume of the joining portion provided on the surface of the second layer" represents the volume of the joining portion located within a range extending in a direction perpendicular to the second layer within the contour of the second layer, and "a volume of the joining portion provided on the surface of the first layer" represents the volume of the joining portion located outside of this range.

In yet another preferred embodiment (5), the ceramic joining unit (1) further comprises a coupling terminal having a plurality of contact surface portions in contact with the joining portion, and when viewed along a lamination direction of the electrode pad, the contour of the second layer, at entire periphery thereof, is located outside respective contours of the contact surface portions, wherein a shortest distance between the contour of the second layer in a short side direction perpendicular to the longitudinal direction and the contours of the contact surface portions is equal to or larger than a maximum length of the contact surface portions in the short side direction.

According to this configuration, the contour of the second layer, at the entire periphery thereof, is located outside of the contours of the contact surface portions when viewed along the lamination direction of the electrode pad. Further, the shortest distance between the contour of the second layer and the contours of the contact surface portions is equal to or larger than the maximum length (maximum width) of the contact surface portions in the short side direction. Thus, the joining portion can be expanded on the surface of the second layer without having to form a joining portion of an excessively large thickness, to thereby join the coupling terminal with the electrode pad (second layer). As a result, exfoliation of the second layer can be suppressed due to stress from the joining portion. Consequently, separation of the coupling terminal from the ceramic base member can be suppressed.

Further, the shortest distance between the contour of the second layer and the contours of the contact surface portions is preferably equal to two times or more of the maximum length (maximum width) of the contact surface portions in the short side direction. Thus, a larger space for expanding the soldering material can be secured on the second layer. As a result, adhesion between the joining portion and the second layer can be further enhanced.

In accordance with a second aspect (6), the present invention, provides a ceramic heater comprising the ceramic joining unit according to the first aspect (1) of the invention; and a heating portion embedded in the leading and side of the ceramic base member and electrically connected to the electrode pad.

Each of the ceramic joining units (1) to (5) above can be embodied as a ceramic heater.

According to a preferred embodiment (7) of the second aspect (6) of the present invention, the second layer has a center of gravity located to the rear of a center of gravity of the first layer.

According to this configuration, the second layer is formed on a rear end side of the first layer. Thus, both the joining portion and the coupling terminal can be separated from the heating portion on the tip end side, so that deterioration due to heat can be suppressed.

The above embodiment (7) can be realized by shifting the second layer to the rear end side with respect to the first layer.

In accordance with a third aspect (8), the present invention provides a gas sensor, comprising: a gas sensor element which includes: a solid electrolyte member configured in a cylindrical shape having a bottom portion and a closed leading end; an outer electrode disposed at an outer peripheral surface of the solid electrolyte member; and an inner electrode disposed at an inner peripheral surface of the solid electrolyte member; and a heater which is inserted into and disposed within the gas sensor element, wherein the heater is the ceramic heater as described in the second aspect (6) of the invention above.

A gas sensor can be embodied so as to include any of the ceramic heaters (6) and (7) above and a gas sensor element.

BRIEF DESCRIPTION OF THE DRAWINGS

Illustrative aspects of the invention will be described in detail with reference to the following figures wherein:

FIG. 9 is a front view of a ceramic heater 100a;

FIG. 10 is a side view of the ceramic heater 100a;

DETAILED DESCRIPTION OF THE PREFERRED EMBODIMENTS

Next, the present invention will be described in greater detail by reference to the drawings. However, the present invention should not be construed as being limited thereto.

A. First Embodiment

A1. Configuration of Gas Sensor

Figure 1:
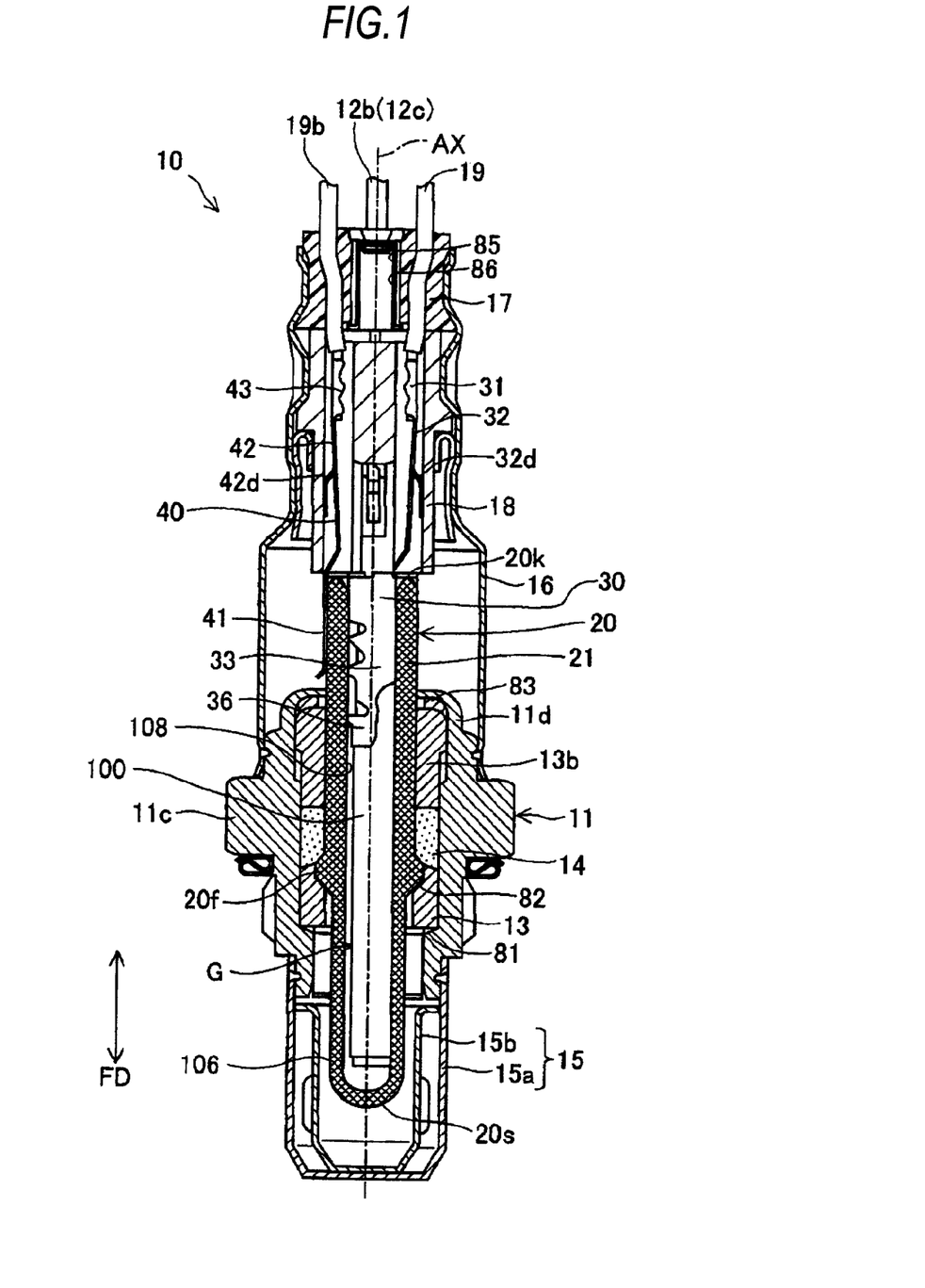
FIG. 1 is a sectional diagram showing the configuration of a gas sensor.

FIG. 1 is a sectional diagram showing the configuration of a first embodiment of the gas sensor of the invention. The gas sensor 10 detects oxygen in the exhaust gas of an internal combustion engine. The gas sensor 10 mainly includes an oxygen detecting element 20, a metal shell 11, an inner terminal member 30, an outer terminal member 40 and a ceramic heater 100.

In FIG. 1, the axis line AX of the gas sensor 10 is shown. Hereinafter, an end portion (lower side in FIG. 1) where a solid electrolyte member 21 is disposed among the both ends of a member extending along the axis line AX is called a tip end and an end portion (upper side in FIG. 1) where a grommet 17 is disposed is called a rear end. The longitudinal direction FD (upper and lower directions in FIG. 1) in the figure represents a direction parallel to the axis line AX.

The oxygen detecting element 20 is configured in a cylindrical shape having a bottom portion in such manner that the element extends in the axis line direction (the upper and lower directions in FIG. 1) along the axis line AX, the tip end 20s (lower side in FIG. 1) is closed and the rear end 20k (upper side in FIG. 1) is open. The oxygen detecting element 20 includes the solid electrolyte member 21 having oxygen ion conductivity, an outer electrode 106 (not shown) formed by electroplating, etc., at a part of the outer peripheral surface of the solid electrolyte member 21, and an inner electrode 108 (not shown) formed by electroplating, etc., at a part of the inner peripheral surface of the solid electrolyte member 21. An engagement flange portion 20f protruding outward is provided at the intermediate portion in the axis direction AX of the outer peripheral surface of the oxygen detecting element 20. The engagement flange portion 20f engages the metal shell 11 as described below.

The metal shell 11 is formed in a cylindrical shape so as to surround a part of the outer periphery of the oxygen detecting element 20. An insulator 13 is disposed via a metal packing 81 (not shown) at the inside of the metal shell 11. The engagement flange portion 20f engages the insulator 13 via a metal packing 82 (not shown). Further, a talc packing 14, an insulator 13b and a metal packing 83 are disposed on the rear end side of the insulator 13, whereby the oxygen detecting element 20 is held in an air-tight state at the inside of the metal shell 11 when crimped at the rear end side of the metal shell 11.

A protector 15 is attached at the tip end side (lower side in FIG. 1) of the metal shell 11. The protector 15 covers the tip end portion of the oxygen detecting element 20 protruding from the tip end side opening portion of the metal shell 11. The protector 15 has a dual structure formed by an outer protector 15a and an inner protector 15b. Each of the outer protector 15a and the inner protector 15b is provided with a plurality of gas transmission ports (not shown) for transferring the exhaust gas therethrough. The exhaust gas is supplied to the outer electrode 106 of the oxygen detecting element 20 via the gas transmission ports of the protector 15.

The metal shell 11 includes a coupling portion 11d at the rear end side (upper side in FIG. 1) of a hexagonal portion 11c formed at the outer periphery thereof. The entire periphery of the tip end of a metal outer cylinder 16 is fixed to the coupling portion 11d from the outside by laser welding. A grommet 17 formed of a fluorine-containing rubber is inserted into an opening on the rear end side of the metal outer cylinder 16. The grommet 17 is fixed by crimping the rear end of the metal outer cylinder 16. The grommet 17 seals the opening of the metal outer cylinder 16. A separator 18 formed of an insulative alumina ceramic is disposed on the tip end side of the grommet 17. Sensor output lead wires 19, 19b and heater lead wires 12b, 12c are disposed so as to penetrate the grommet 17 and the separator 18. A through hole is formed along the axis line AX at the center of the grommet 17 and a metal pipe 86 is fit into the through hole. A filter 85 of a sheet shape having water repellency and air permeability covers the metal pipe 86. Thus, the atmosphere at the outside of the gas sensor 10 is introduced into the metal outer cylinder 16 via the filter 85 and further within the inner space G of the oxygen detecting element 20.

The outer terminal member 40 includes an outer fitting portion 41 formed of a stainless steel plate, a separator insertion portion 42 and a connector portion 43. The separator insertion portion 42 is inserted within the separator 18. A separator abutment portion 42d is branched from the separator insertion portion 42 and protrudes therefrom. Since the separator abutment portion 42d elastically contacts the inner wall of the separator 18, the outer terminal member 40 is held within the separator 18.

The connector portion 43 is provided at the rear end of the separator insertion portion 42. The connector portion 43 grasps the core wire of the sensor output lead wire 19b upon being crimped to thereby electrically connect the outer terminal member 40 and the sensor output lead wire 19b.

The outer fitting portion 41 is provided at the tip end of the separator insertion portion 42. The outer fitting portion 41 grasps the outer periphery near the rear end of the oxygen detecting element 20 to thereby electrically connect the outer terminal member 40 and the outer electrode 106 of the oxygen detecting element 20.

The inner terminal member 30 includes an insertion portion 33 formed by a stainless steel plate, a separator insertion portion 32 and a connector portion 31. The separator insertion portion 32 is inserted within the separator 18. A separator abutment portion 32d is branched from the separator insertion portion 32 and protrudes therefrom. Since the separator abutment portion 32d elastically contacts the inner wall of the separator 18, the inner terminal member 30 is held within the separator 18.

The connector portion 31 is provided at the rear end of the separator insertion portion 32. The connector portion 31 grasps the core wire of the sensor output lead wire 19 upon being crimped to thereby electrically connect the inner terminal member 30 and the sensor output lead wire 19.

The insertion portion 33 is provided at the tip end of the separator insertion portion 32. The insertion portion 33 is inserted within the oxygen detecting element 20. The portion 33 contacts the inner electrode 108 formed at the inner peripheral surface of the so as to press against the inner electrode by its own elastic force. In this manner, the insertion portion 33 is held in electrical contact with the inner electrode 108 of the oxygen detecting element 20.

A heater pressing portion 36 is provided at the tip end of the insertion portion 33. The heater pressing portion 36 presses the side surface of the ceramic heater 100 against the inner peripheral surface of the oxygen detecting element 20.

The ceramic heater 100 is disposed within the inner space G and held by the inner terminal member 30 to thereby maintain its posture. The ceramic heater 100 is configured such that a coupling terminal 130 described below is electrically connected to the heater lead wires 12b, 12c and electric power is supplied via the heater lead wires 12b, 12c to thereby heat the solid electrolyte member 21.

A2. Configuration of Ceramic Heater

Figure 2:
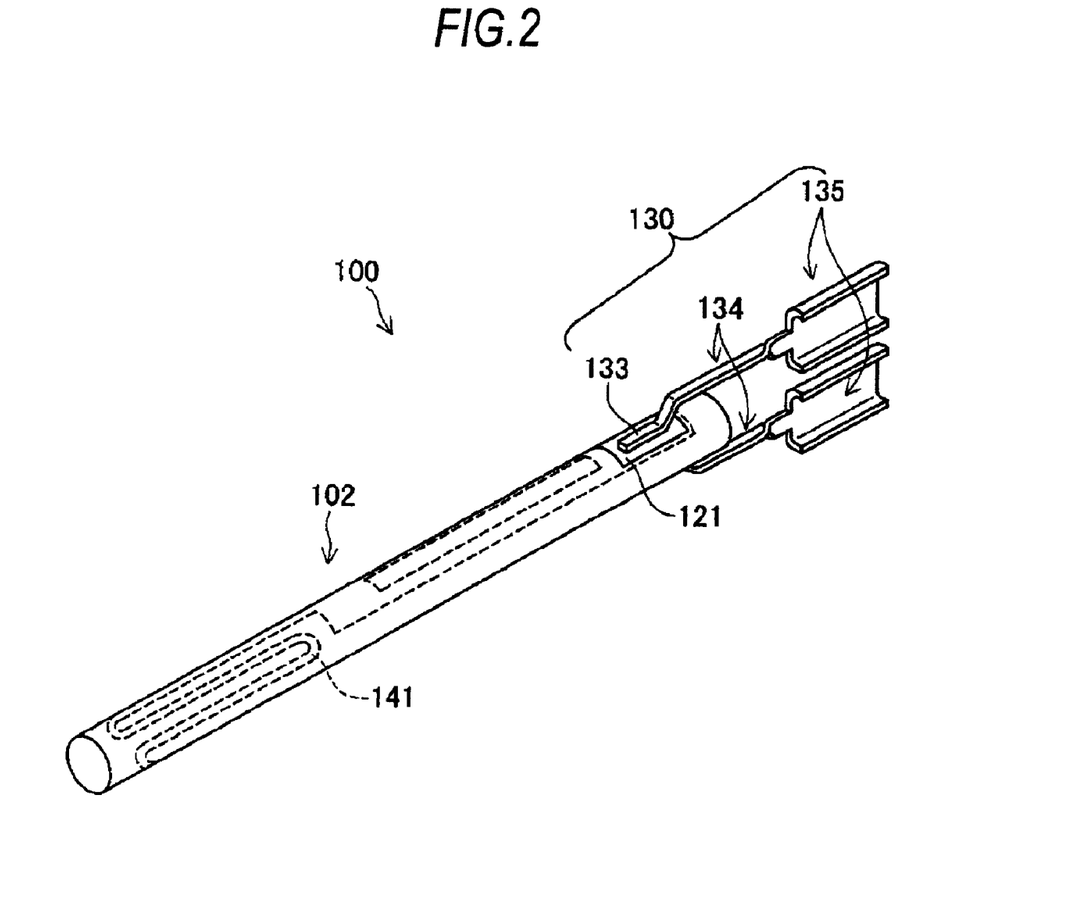
FIG. 2 is a perspective view of the ceramic heater.
Figure 3:
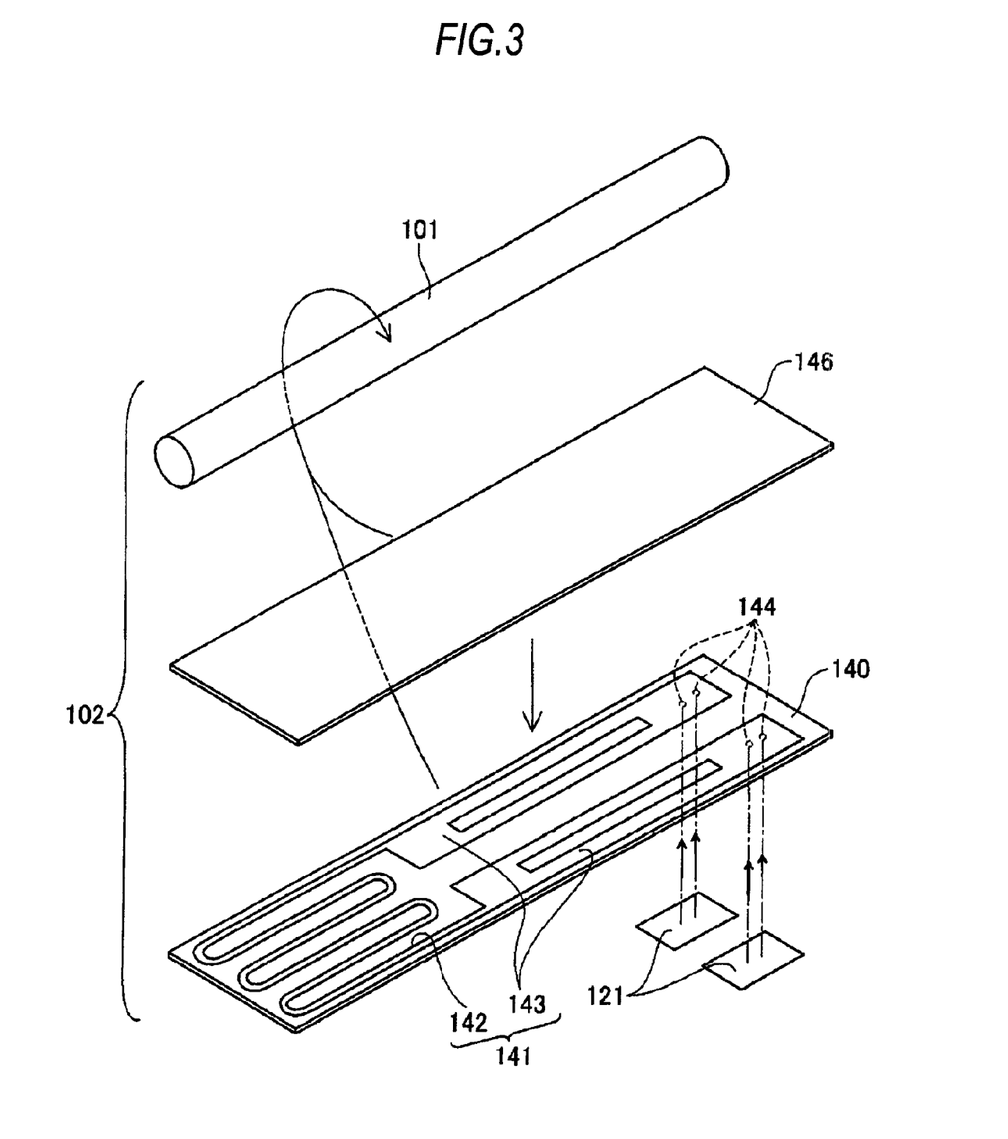
FIG. 3 is a broken perspective view showing the inner configuration of the ceramic heater.

FIG. 2 is a perspective view of the ceramic heater. FIG. 3 is an exploded perspective view showing the inner configuration of the ceramic heater. As shown in FIG. 2, the ceramic heater 100 is configured by fixing the coupling terminal 130 to a ceramic base member 102 having a round rod shape (φ3 mm and an entire length of 50 mm in this embodiment). As shown in FIG. 1, the ceramic heater 100 is inserted into the oxygen detecting element 20 to thereby heat the oxygen detecting element 20. Among the both end sides in the longitudinal direction of the ceramic heater 100, a side (left side in FIG. 2) having a heating portion is hereinafter called "a tip end side" and the opposite side thereof is called "a rear end side".

The ceramic heater 100 includes the ceramic base member 102, an electrode pad 121 and the coupling terminal 130. As shown in FIG. 3, the ceramic base member 102 is fabricated such that green sheets 140, 146 each formed of a highly insulating alumina ceramic, are wound around the outer periphery of a porcelain tube 101 having a round shape (columnar shape) formed of an alumina ceramic, and this assembly is then sintered.

A heating resistor 141 (heater pattern) is formed on the green sheet 140. The heater resistor 141 includes a heating portion 142 and a pair of lead portions 143 (a positive electrode and a negative electrode) respectively connected to the both ends of the heating portion 142. The material of the heating portion 141 may be one of various kinds of conductive material such as tungsten or molybdenum. Two through holes 144 are provided at the rear end side of the green sheet 140 corresponding to the lead portions 143, respectively. The electrode pads 121 formed on the outer surface of the ceramic heater 100 are electrically connected to the lead portions 143, respectively.

The green sheet 146 is in contact with and pressed against the surface of the green sheet 140 on which the heating resistor 141 is formed. A ceramic heater member is formed such that an alumina paste is pasted on the contact surface and the opposite surface of the green sheet 146. The green sheets 140, 146 are wound around the porcelain tube 101 such that the pasted surface is directed to the inner side and the green sheets are pressed toward the inside from the outer periphery side. Thereafter, the ceramic heater member is sintered to thereby form the ceramic base member 102.

As shown in FIGS. 2 and 3, the two electrode pads 121 configured by the electrode pad 121 of the positive electrode side and the electrode pad 121 of the negative electrode side are formed on the surface of the ceramic base member 102. These electrode pads 121 are provided at portions on the outer surface of the green sheet 140 where the through holes 144 are formed, respectively. Electrical connection between the lead portion 143 and the electrode pad 121 on each of the positive and negative electrode sides is made by a conductive paste filled into the through hole 144.

Figure 4:
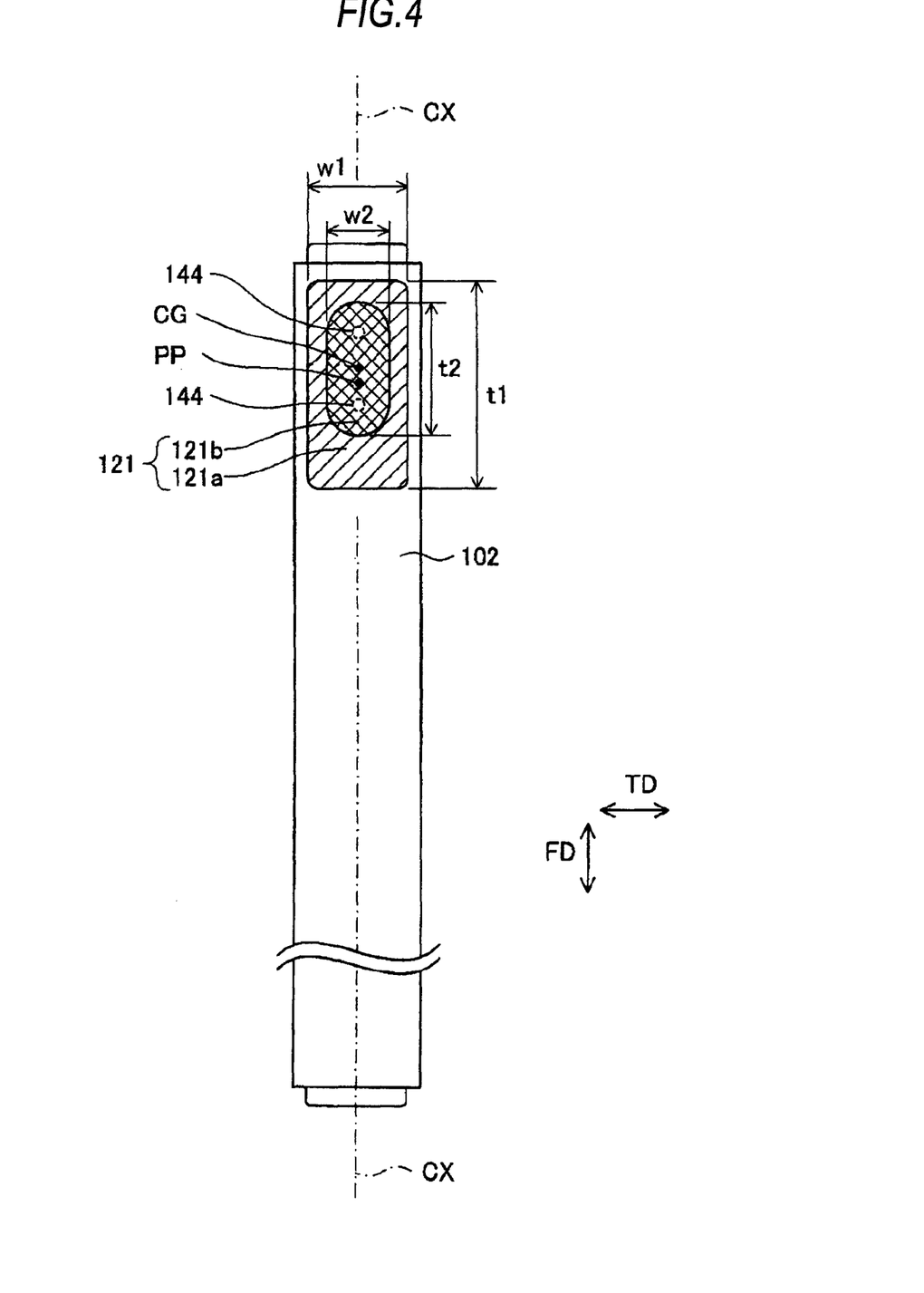
FIG. 4 is a front view of a ceramic base member 102.

FIG. 4 is a front view of the ceramic base member 102. This front view is a diagram of the ceramic base member 102 which is seen along a direction perpendicular to the center axis CX (also called a lamination direction ND hereinafter (see FIG. 6 described below)) of the ceramic base member 102. A longitudinal direction FD is a direction parallel to the center axis CX. A short side direction TD is a direction perpendicular to both the longitudinal direction FD and the lamination direction ND. This is a front view of one of the two electrode pads 121 disposed at the ceramic heater.

Figure 5:
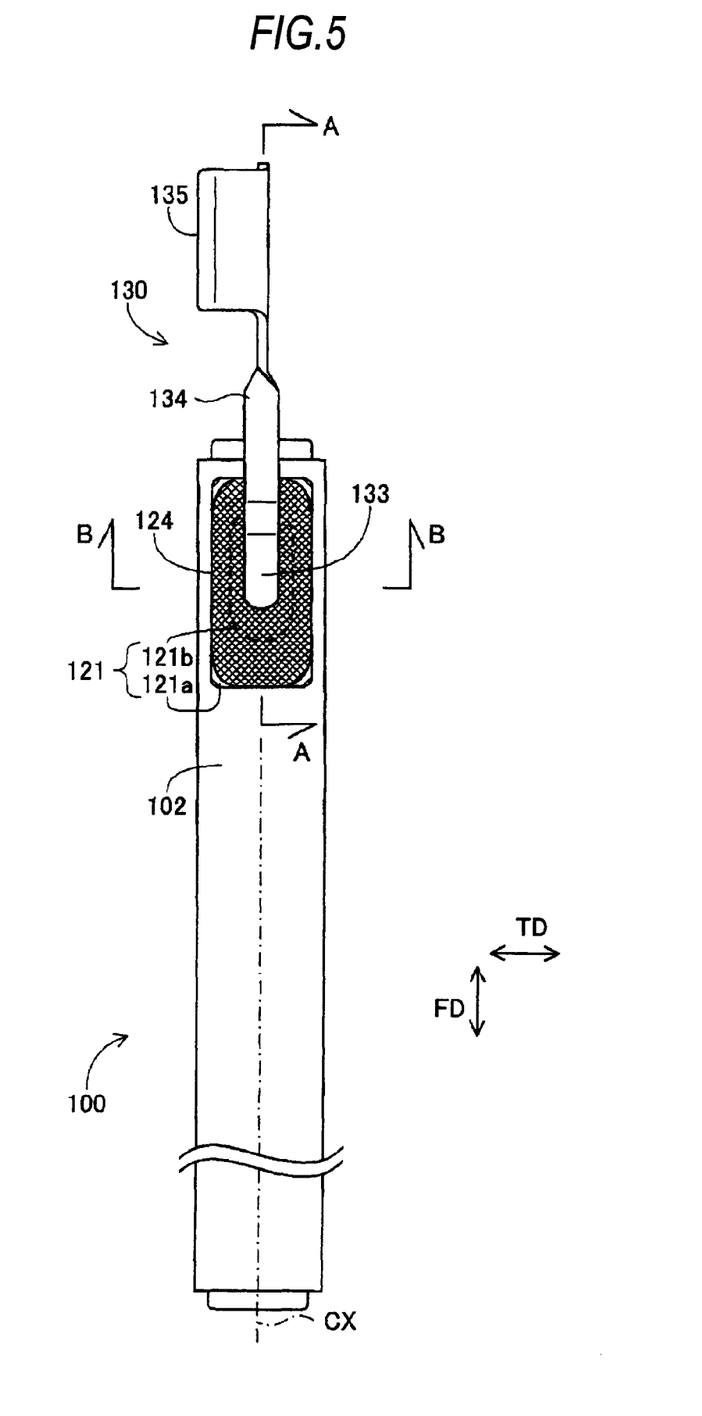
FIG. 5 is a front view of the ceramic heater 100.

FIG. 5 is a front view of the ceramic heater 100. This front view shows a state where the ceramic base member 102 shown in FIG. 4 is fixed to the coupling terminal 130. The coupling terminal 130 is disposed so as to extend parallel to the center axis 130 and the joining end portion 133 thereof is fixed to the electrode pad 121 by means of a solder joint.

Figure 6:
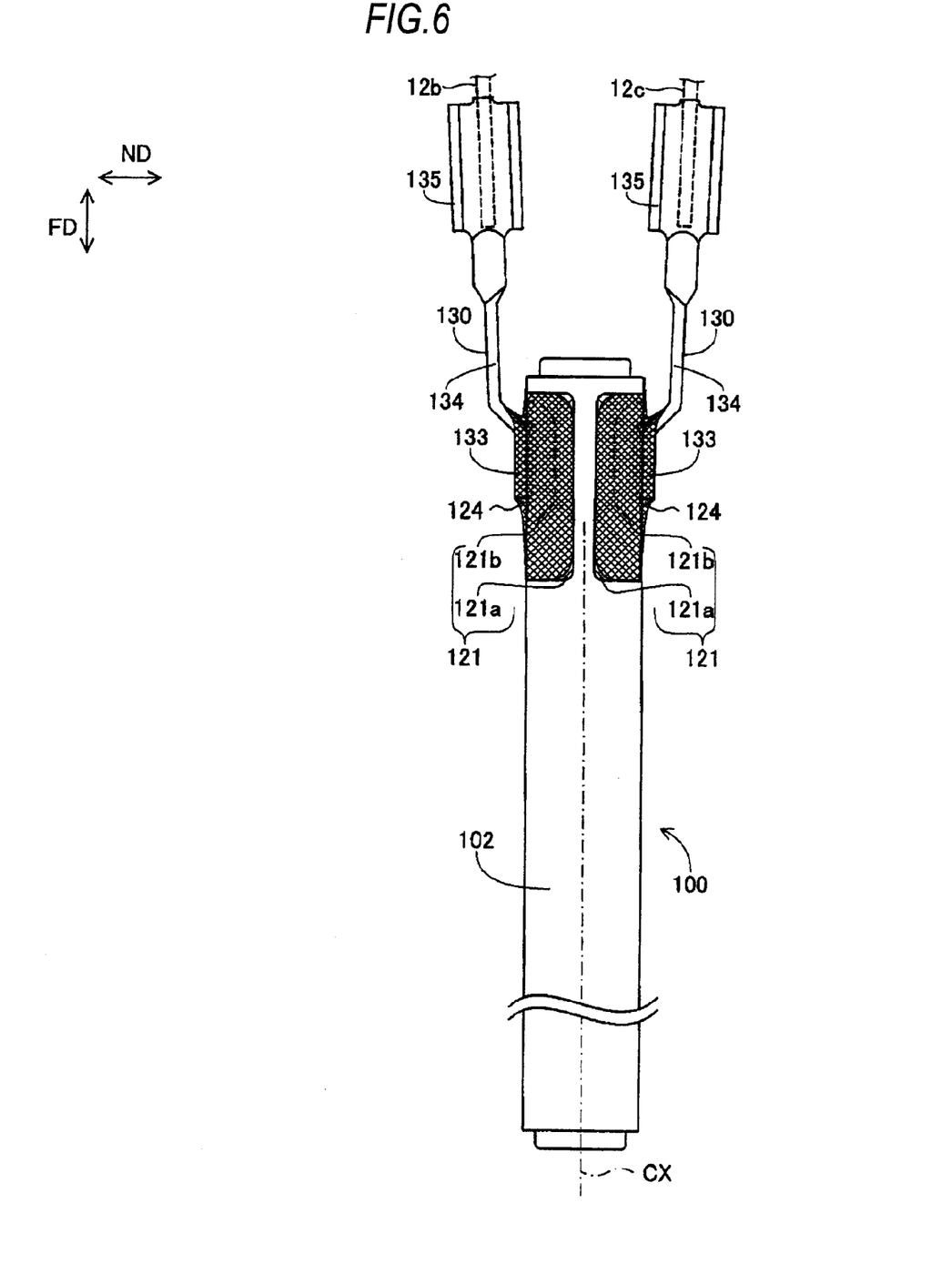
FIG. 6 is a side view of the ceramic heater 100.

FIG. 6 is a side view of the ceramic heater 100. This side view is a diagram of the ceramic heater as shown in the front view of FIGS. 4 and 5 but viewed from a direction rotated by 90 degrees with respect to the center axis CX (as seen along the short side direction TD).

Figure 7:
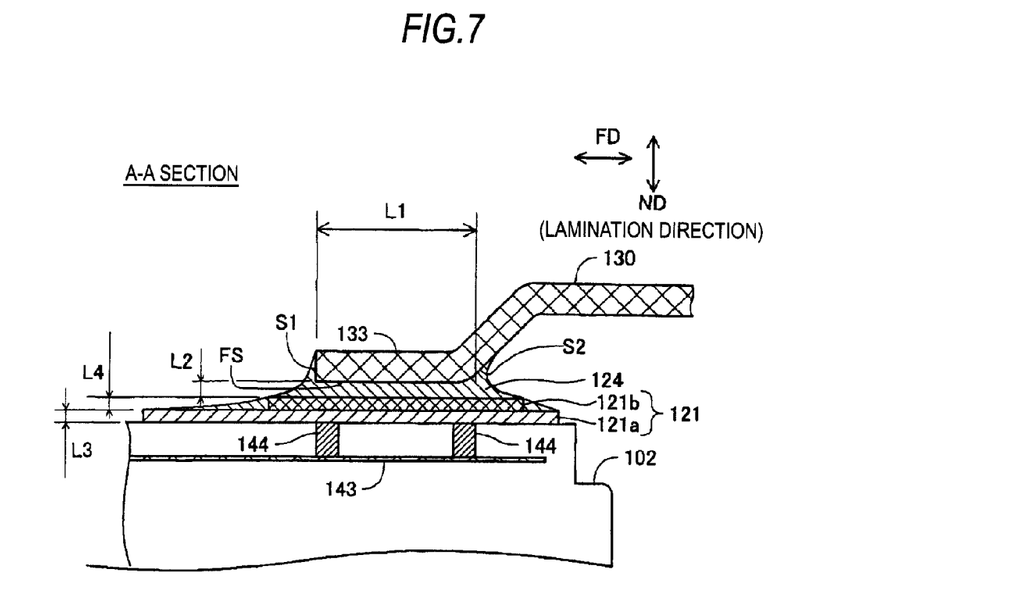
FIG. 7 is a sectional diagram cut along a line A-A.
Figure 8:
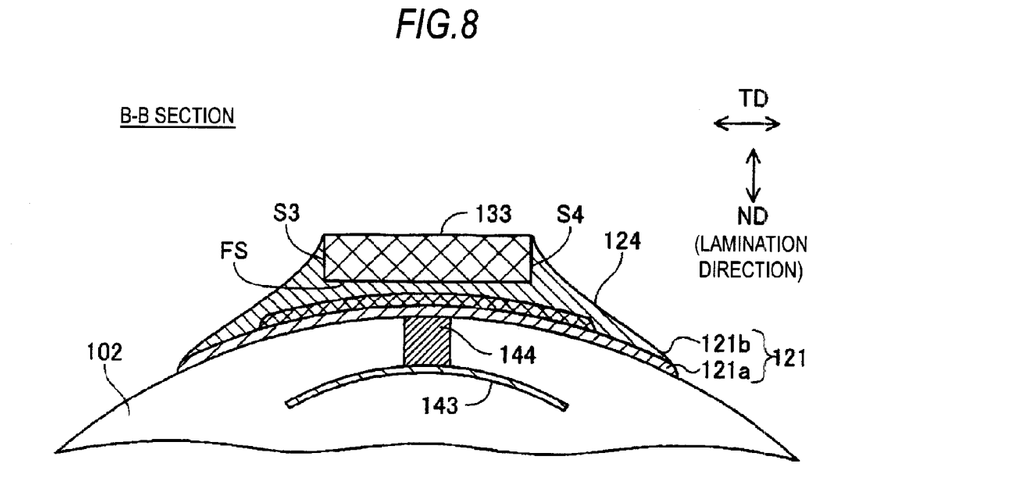
FIG. 8 is a sectional diagram cut along a line B-B.

FIG. 7 is a diagram of the ceramic heater cut along a line A-A shown in FIG. 5 (a sectional diagram including the center axis CX). FIG. 8 is a diagram of the ceramic heater cut along a line B-B shown in FIG. 5 (a sectional diagram perpendicular to the center axis CX). Each of FIGS. 7 and 8 shows a portion of the ceramic heater near the electrode pad 121. As shown in these figures, the electrode pad 121 is formed on the surface of the ceramic base member 102. Further, the electrode pad 121 is connected to the lead portion 143 via the through hole 144

As shown in FIGS. 4, 7 and 8, the electrode pad 121 includes a first layer 121a in contact with the ceramic base member 102 and a second layer 121b laminated on the first layer 121a.

The main component of the first layer 121a is tungsten. Further, the first layer 121a contains alumina (aluminum oxide) as a ceramic material which is the main component of the ceramic base member 102. The content of the alumina in the first layer 121a is preferably set in a range from 2 to 20 wt %. Accordingly, adhesion between the first layer 121a and the ceramic base member 102 can be improved without excessively degrading the conductivity of the first layer 121a. As a result, exfoliation of the first layer 121a from the ceramic base member 102 can be suppressed. In this embodiment, 90 wt % W (tungsten)-10 wt % $Al_2O_3$ is employed as the first layer 121a.

Similarly, the main component of the second layer 121b is tungsten. The second layer 121b also contains alumina as a ceramic material which is the main component of the ceramic base member 102. The amount of the alumina in the second layer 121b is set so as to be less than that of the first layer 121a. When the content of the alumina is small, some of the soldering material is likely to migrate into the second layer 121b. As a result, adhesion between the second layer 121b and the soldering material can be improved. The content of alumina in the second layer 121b is preferably set in a range from 0 to 10 wt %. That is, the second layer 121b need not contain alumina. In this case, the amount of alumina in the first layer 121a is greater than that of the second layer 121b. In this embodiment, the second layer 121b is 100 wt % W (tungsten).

As described above, in this embodiment, an electrode pad 121 having a multi-layer structure is employed which is arranged such that the content of the ceramic material as the main component of the ceramic base member 102 is reduced with an increase in distance from the ceramic base member 102. Thus, adhesion between the electrode pad 121 and the ceramic base member 102 is improved. Also, adhesion between the electrode pad 121 and a joining portion 124 is improved.

Next, the shape of each of the layers 121a and 121b will be explained. As shown in FIG. 4, in this embodiment, the first layer 121a seen along the lamination direction ND has a substantially rectangular shape having a height t1 of 5.0 mm and a width w1 of 2.4 mm (the height represents a length in the longitudinal direction FD, the width represents a length in the short side direction TD, and each of the four corners is rounded). The second layer 121b seen along the lamination direction has a substantially rectangular shape having a height t2 of 3.2 mm and a width w2 of 2.2 mm (each of the four corners is rounded).

As shown in FIG. 4, when the electrode pad 121 is viewed along the lamination direction, the contour of the first layer 121a is located on the outer side of the contour of the second layer 121b along the entire periphery of the first layer. That is, the entire contour of the second layer 121b is located on the inner side of the contour of the first layer 121a. As a result, the area of the second layer 121b is smaller than that of the first layer 121a, such that the first layer 121a is exposed along the entire periphery of the second layer 121b. Thus, the second layer 121b is not provided directly on the ceramic base member 102. In this manner, the entire edge of the second layer 121b can be joined firmly with the first layer 121a, whereby exfoliation of the second layer 121b from the first layer 121a can be suppressed.

Further, as shown in FIG. 4, the center of gravity CG of the second layer 121b is set so as to be located on the rear end side relative to the center of gravity PP of the first layer 121a. In other words, the second layer 121b is disposed so as to be shifted on the rear end side with respect to the first layer 121a. In this manner, the joining portion 124 and the coupling terminal 130 can be further separated from the heating portion 142, and so the degradation thereof due to heat can be suppressed.

FIGS. 5 and 6 show the coupling terminal 130. Each of the coupling terminals 130 is formed of a nickel alloy. Each of the coupling terminals 130 includes a coupling portion 134, the joining end portion 133 provided at one end of the coupling portion 134, and a crimping portion 135 provided at the other end of the coupling portion 134. As shown in FIG. 6, the one end of the coupling portion 134 is bent in a step manner in the lamination direction and coupled to the joining end portion 133. As shown in FIG. 5, the joining end portion 133 is disposed at substantially the center of the second layer 121b and soldered. The length L1 (see FIG. 7) of each of the joining end portions 133 is 2.0 mm in this embodiment.

The crimping portion 135 is formed of a flat plate having a width larger than that of the coupling portion 134. The coupling part between the coupling portion 134 and the crimping portion 135 is bent so as to be twisted by about 90 degrees around the longitudinal direction of the coupling portion 134. Both ends of the crimping portion 135 are bent to the same side. The two crimping portions 135 hold the core wires of the heater lead wires 12b, 12c by crimping to thereby electrically connect the heating resistor 141 to the heater lead wires 12b, 12c, respectively.

Further, as shown in FIGS. 5 to 8, the coupling terminal 130 is fixed to the second layer 121b and the first layer 121a by means of a solder joint. The joining portion 124 for joining the coupling terminal 130 with the second layer 121b is formed by soldering. The joining portion 124 is formed by solidifying the soldering material. In this embodiment, an Au—Cu alloy (alloy of gold and copper) is used as the soldering material.

FIGS. 7 and 8 show the detailed configuration of the solder joint. The joining end portion 133 is disposed so as to be substantially parallel to the electrode pad 121 (second layer 121b). The joining end portion 133 may contact the second layer 121b or a gap may be formed between members 133 and 121b (a gap L2 therebetween is set to be in a range from 0 to 0.5 mm in this embodiment).

As shown in FIGS. 7 and 8, of the surfaces of the joining end portion 133, a surface FS opposing to the second layer 121b and surfaces S1 to S4 adjacent to the surface FS are disposed so as to contact the joining portion 124. The joining portion 124 is configured such that the soldering material thereof expands in a fillet shape toward the second layer 121b and the first layer 121a from the joining end portion 133.

Since the joining portion 124 is provided so as to expand over the second layer 121b to the surface of the first layer 121a, the joining area between the joining portion 124 and the electrode pad 121 is increased. In this manner, the joining portion 124 can be firmly joined to the electrode pad 121. Further, the joining portion 124 is provided so as to cover the portion 121b. Thus, an outside impact, etc., is not directly applied to the second layer 121b, so that the second layer 121b does not become separated from the first layer 121a.

As shown in FIGS. 5 and 6, the joining portion 124 is provided so that at least a part of the surface of the first layer 121a is exposed. That is, the joining portion 124 is not provided on a part of the surface of the first layer 121a.

Further, as shown in FIGS. 7 and 8, a volume of the joining portion 124 provided on the surface of the first layer 121a is set to be smaller than that of the joining portion 124 provided on the surface of the second layer 121b. Thus, the ceramic material within the first layer 121a can be suppressed from migrating into the joining portion 124. In this manner, adhesion between the joining portion 124 and the electrode pad 121 can also be improved while maintaining adhesion between the joining portion 124 and the first layer 121a.

In this embodiment, the thickness L3 of the first layer 121a is set to be 30 μm and the thickness L4 of the second layer 121b is set to be 25 μm (see FIG. 7). In this manner, the first layer 121a is thicker than the second layer 121b. Thus, adhesion between the first layer 121a and the ceramic base member 102, which materials considerably differ from each other, can be sufficiently maintained and exfoliation of the first layer 121a from the ceramic base member 102 can be suppressed. On the other hand, since the second layer 121b is thinner than the first layer 121a, the stress imparted to the second layer can be reduced. In this manner, adhesion between the first layer 121a and the second layer 121b and also adhesion between the second layer 121b and the joining portion 124 can be further improved.

The ceramic heater 100 is provided with two pairs (positive electrode and negative electrode) of the electrode pads 121 and the coupling terminals 130. The configuration of the electrode pads 121 and the joining state between the electrode pad 121 and the coupling terminal 130 is the same for both pairs. The configuration of the coupling terminal 130 is the same for both pairs except for the direction of the crimping portion 135.

As described above, according to the first embodiment, separation between each of the ceramic base member 102 and the first layer 121a, the first layer 121a and the second layer 121b, the second layer 121b and the joining portion 124, and the second layer 121b and the coupling terminal 130 is suppressed. Thus, separation between the coupling terminal 130 and the ceramic base member 102 can be suppressed.

In this embodiment, the entirety of the ceramic base member 102, the electrode pad 121, the joining portion 124 and the coupling terminal 130 correspond to the "ceramic joining unit" of the invention.

Well known various kinds of methods may be selectively employed for fabricating the ceramic heater 100. For example, the following method may be employed. That is, first, the heating resistor 141 and the electrode pad 121 are formed by coating an ink containing conductive material on the surface of the green sheet 140. Various techniques such as screen printing may be selectively employed as the technique for coating the ink. In this case, the first layer 121a may be formed on the green sheet 140 and thereafter the second layer 121b may be formed on the first layer 121a. Conductive paste is filled into the through hole 144. Then, the green sheet 146 is laminated on the green sheet 140. Next, the green sheets 140, 146 are wound around the porcelain tube 101, and the resulting assembly is sintered to thereby form the ceramic base member 102. Then, the coupling terminal 130 is fixed to the electrode pad 121 by soldering. Various methods may be selectively employed as the soldering technique. For example, first, the joining end portion 133 is disposed at a position opposite the second layer 121b. Then, soldering material melted by heating is caused to flow so as to cover the joining end portion 133 and the second layer 121b. Then, the soldering material is cooled and solidified to thereby fix the coupling terminal 130 to the electrode pad 121. The surface of the second layer 121b may be electroplated with a metal such as nickel before soldering so as to promote migration of the soldering material into the second layer 121b.

Also, various well known methods may be selectively employed as a method of fabricating the gas sensor 10.

B. Second Embodiment

Figure 9:
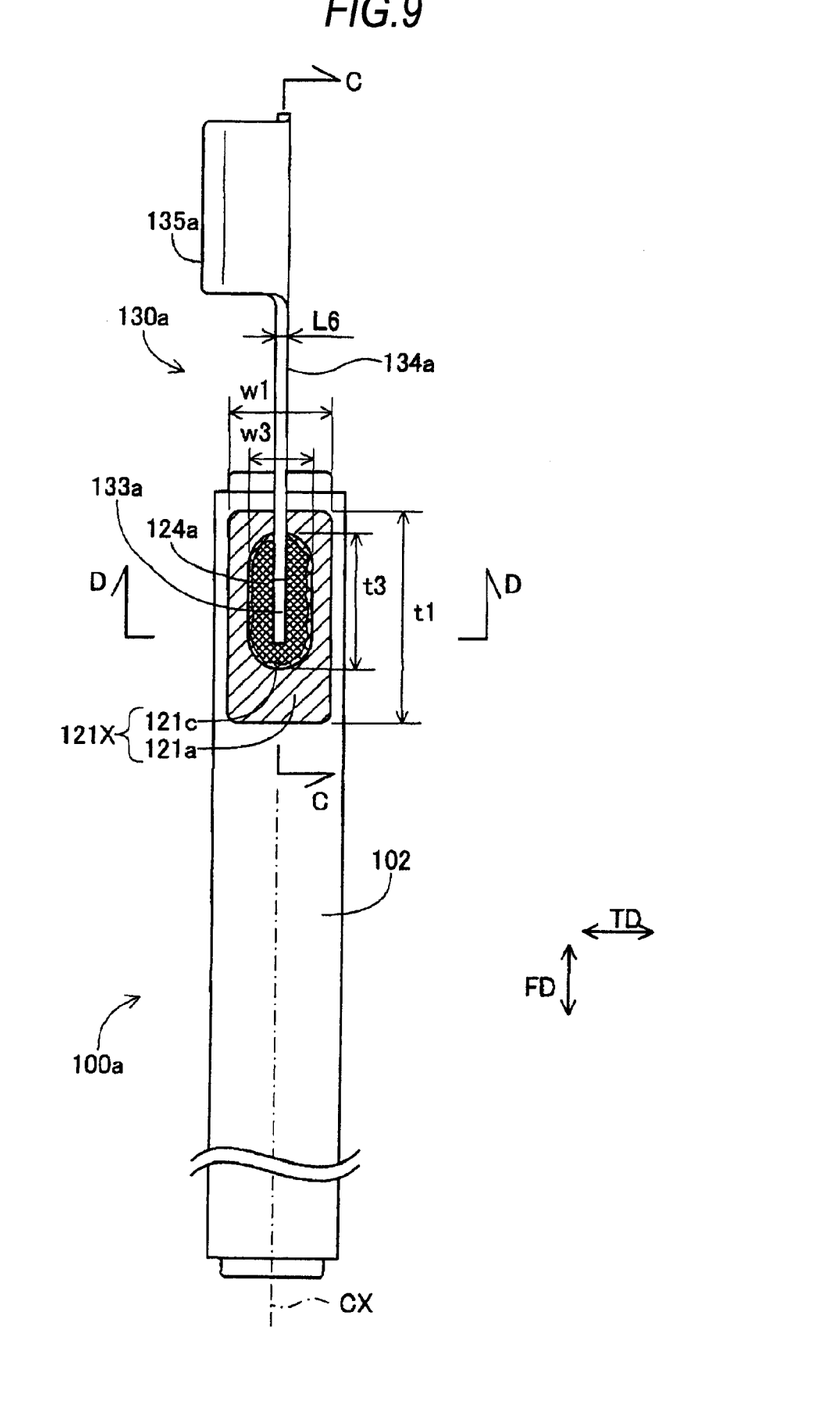
Figure 10:
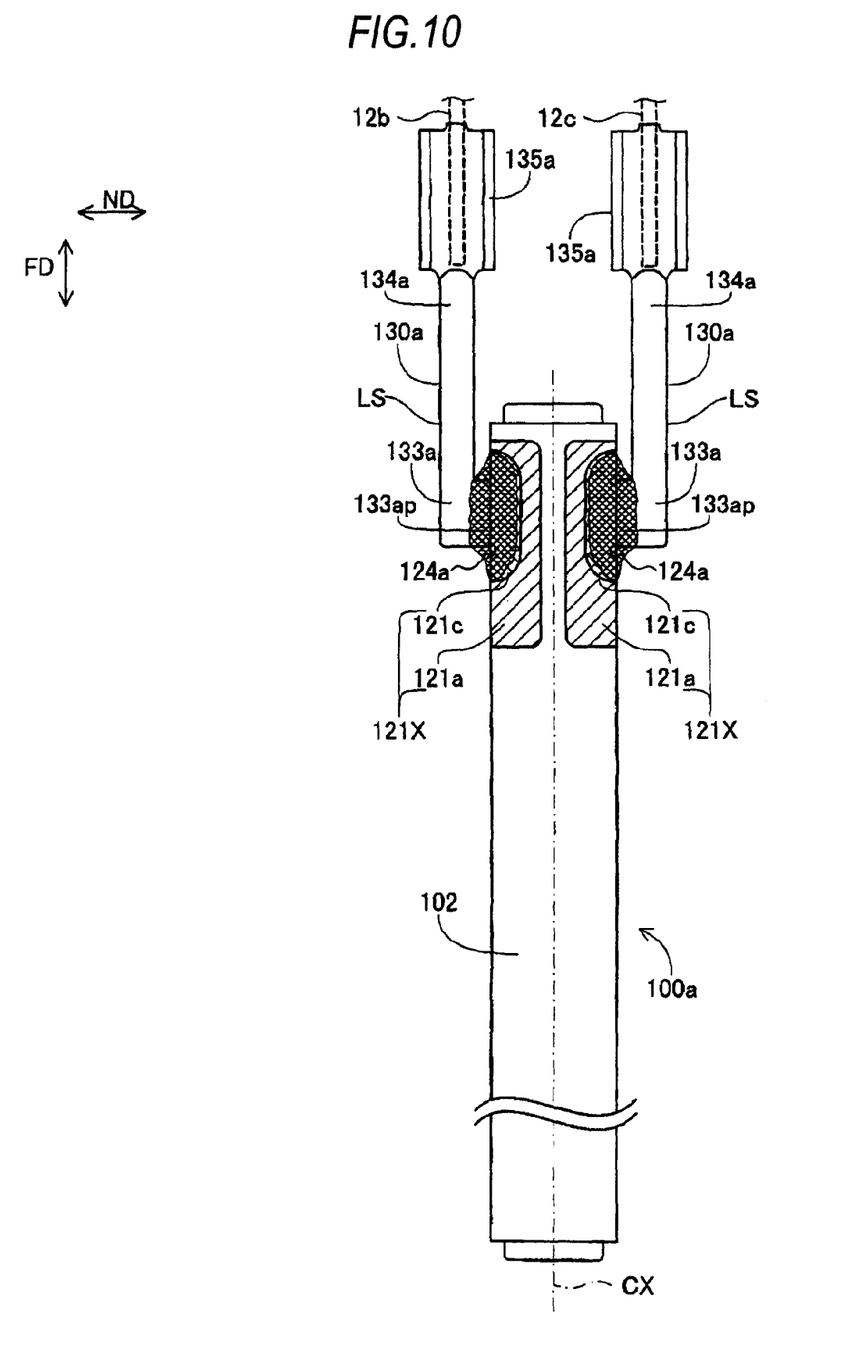

FIGS. 9 and 10 are diagrams illustrating another embodiment of the ceramic heater. This embodiment differs from the first embodiment shown in FIGS. 5 and 6 in the following three points. Firstly, the shape of coupling terminal 130a differs from the shape of the coupling terminal 130 of the first embodiment. Secondly, the shape of second layer 121c differs from the shape of the second layer 121b of the first embodiment (hereinafter an electrode pad having the first layer 121a and the second layer 121c is called an electrode pad 121X). Thirdly, the shape of joining portion 124a between the coupling terminal 130a and the electrode pad 121X (second layer 121c) differs from the shape of the joining portion 124 of the first embodiment. The remaining configuration of this embodiment is same as that of the first embodiment. FIG. 9 shows a front view of the ceramic heater similar to FIG. 5, and FIG. 10 shows a side view thereof similar to FIG. 6.

The configurations of the ceramic base member 102 and the electrode pad 121X in this embodiment are same as the ceramic base member 102 and the electrode pad 121 of the first embodiment shown in FIGS. 2 to 4, respectively. Thus, the ceramic heater 100a of the second embodiment has various advantages similar to the ceramic heater 100 of the first embodiment.

The coupling terminal 130a is disposed so as to extend parallel to the center axis CX and the joining end terminal 133a is fixed to the electrode pad 121X by means of a solder joint. The ceramic heater 100a can be used in place of the ceramic heater 100 of the first embodiment.

In the second embodiment, each of the coupling terminals 130a includes a coupling portion 134a, a joining end portion 133a provided at the one end of the coupling portion 134a, and a crimping portion 135a provided at the other end of the coupling portion 134a. Each of the joining end portion 133a and the coupling portion 134a is formed of a flat plate with a thickness L6 (see FIG. 9) of 0.3 mm. As shown in FIG. 10, the entirety of the joining end portion 133a and the coupling portion 134a has an L-shape. The joining end portion 133a is a rectangular flat plate having a length L5 (see FIG. 11) of 2.0 mm. The one long side of the coupling portion 134a and the one long side of the joining end portion 133a are located on a common line LS. The end portion 133ap of the joining end portion 133a on the side opposite the line LS protrudes inwardly as viewed from the coupling portion 134a side.

The coupling terminals 130a is disposed such that the protruded portion 133ap opposes the electrode pad 121X (second layer 121c) (see FIG. 10). The joining end portion 133a is disposed substantially at the center of the second layer 121c (see FIG. 9). As described below, the joining end portion 133a is disposed so as to be substantially orthogonal to the electrode pad 121X (second layer 121c). In this state, the joining end portion 133a is soldered to the electrode pad 121X (second layer 121c).

The crimping portion 135a is connected to the other end of the coupling portion 134a. The configuration of the crimping portion 135a is same as that of the crimping portion 135 shown in FIGS. 5 and 6. The two crimping portions 135a hold the core wires of the heater lead wires 12b, 12c by crimping to thereby electrically connect the heating resistor 141 (FIG. 3) with the heater lead wires 12b, 12c, respectively.

Figure 11:
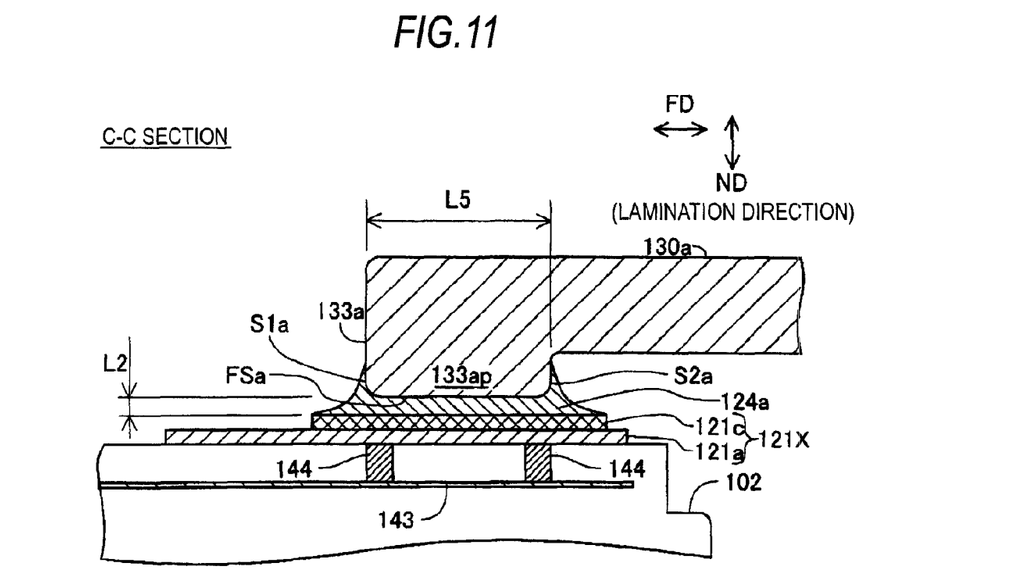
FIG. 11 is a sectional diagram cut along a line C-C.
Figure 12:
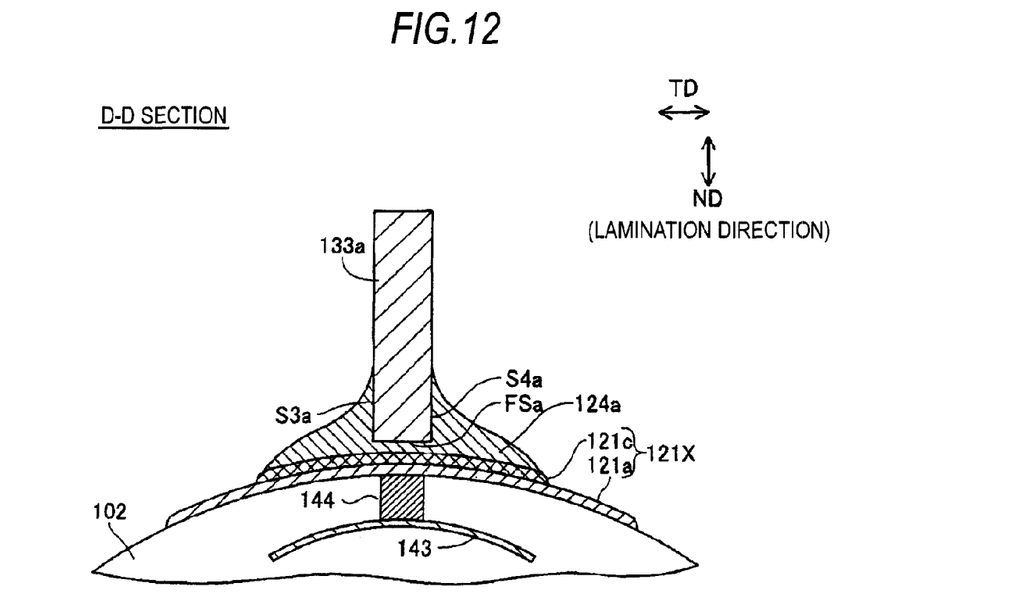
FIG. 12 is a sectional diagram cut along a line D-D.

FIGS. 11 and 12 show a detailed configuration of the solder joint. FIG. 11 shows a sectional diagram (sectional diagram along the center axis CX) of the soldered portion cut along a line C-C in FIG. 9 and FIG. 12 shows a sectional diagram (sectional diagram perpendicular to the center axis CX) of the soldered portion cut along a line D-D in FIG. 9. Each of FIGS. 11 and 12 shows a portion near the electrode pad 121X.

The coupling terminal 130a is fixed to the second layer 121c by means of a solder joint. The joining portion 124a for joining the coupling terminal 130a with the second layer 121c is formed by soldering. The joining portion 124a is formed by solidifying the soldering material.

As shown in FIGS. 11 and 12, the joining end portion 133a is disposed so as to be substantially perpendicular to the electrode pad 121X (second layer 121c) (that is, the joining end portion 133a is substantially parallel to the lamination direction of the electrode pad 121X). The surface of the joining end portion 133a opposing the second layer 121c forms the surface FSa of the end portion 133ap thereof. The surface FSa is parallel to both the long side of the joining end portion 133a and the thickness direction of the joining end portion 133a. The surface FSa is substantially parallel to the electrode pad 121X (second layer 121c). The joining end portion 133a may be in contact with the second layer 121c, or these members may be separated by a gap L2 set in a range of from 0 to 0.2 mm in this embodiment.

As shown in the drawings, of the surfaces of the joining end portion 133a, the surface FSa and surfaces S1a to S4a adjacent to the surface FSa are disposed so as to contact the joining portion 124a. The joining portion 124a is configured such that the soldering material thereof expands in a fillet shape toward the peripheral edge of the second layer 121c from the joining end portion 133a.

Figure 13:
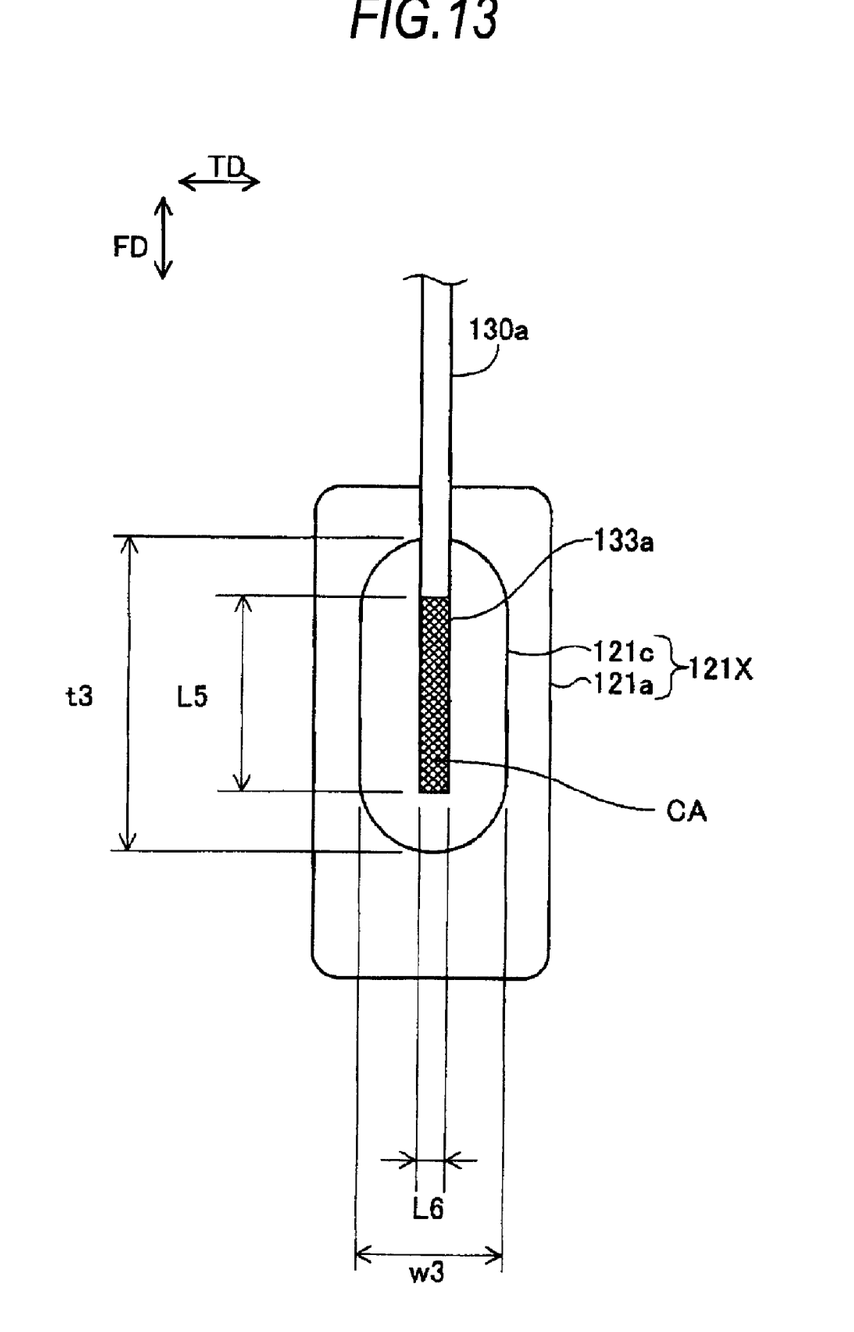
FIG. 13 is a diagram illustrating a joining state.

FIG. 13 is a diagram illustrating the joining state between the joining end portion 133a and the electrode pad 121X. FIG. 13 is an enlarged diagram of a portion near the electrode pad 121X in FIG. 9. This figure is a front view showing a part of the coupling terminal 130a and the electrode pad 121X.

A hatched area CA shows a contact surface portion CA. The contact surface portion CA represents a portion of the surface of the coupling terminal 130a which directly contacts the joining portion 124a (FIGS. 11 and 12). In this embodiment, of the entire surfaces FSa, S1a, S2a, S3a and S4a, the portion contacting the joining portion 124a corresponds to the contact surface portion CA.

In this embodiment, the contact surface portion CA forms a rectangular area when viewed along the lamination direction ND of the electrode pad 121X. The width (length in the short side direction TD) L6 of the contact surface portion CA is 0.3 mm and the height L5 (length toward the tip end direction FD) is 2.0 mm. Further, the width w3 of the second layer 121c is 1.5 mm and the height t3 thereof is 3.2 mm. The contact surface portion CA is disposed substantially at the center of the second layer 121c. As a result, the second layer 121c protrudes outwardly by 0.6 mm at the entire periphery of the contact surface portion CA.

That is, when viewed along the lamination direction ND of the electrode pad 121X, the contour of the second layer 121c is located at the outside of the contour of the contact surface portion CA on the entire periphery thereof. The shortest distance (0.6 mm in this embodiment) between the contour of the second layer 121c and the contour of the contact surface portion CA in the short side direction TD perpendicular to the longitudinal direction FD is equal to or greater than the maximum length (0.3 mm in this embodiment) of the contact surface portion CA in the short side direction TD. As a result, sufficient space for expanding the soldering material can be secured on the second layer 121c along the entire periphery of the contact surface portion CA. Thus, adhesion between the joining portion 124a (FIGS. 11 and 12) and the second layer 121c can be enhanced. Further, the coupling terminal 130a and the electrode pad 121X (second layer 121c) can be joined to each other without having to provide an excessively thick joining portion 124a on the second layer 121c. As a result, exfoliation of the second layer 121c can be suppressed due to stress on the joining portion 124a. The distance between the contour of the second layer 121c and the contour of the contact surface portion CA in the short side direction TD may be changed in accordance with the position in the longitudinal direction FD. Similarly, the length of the contact surface portion CA in the short side direction TD may also be changed in accordance with the position in the longitudinal direction FD.

The ceramic heater 100a is provided with two pairs (positive electrode and negative electrode) of the electrode pads 121X and the coupling terminals 130a. The configuration of the electrode pads 121X and the joining state between the electrode pad 121X and the coupling terminal 130a is the same for both pairs. The configuration of the coupling terminal 130a is the same for both pairs except for the direction of the crimping portion 135a.

C. Modified Example

The invention is not limited to the aforesaid embodiments, and various modes may be implemented within a scope not departing from the gist of the invention. For example, the invention may be implemented in the following modified examples.

In the respective embodiments, the configuration of the ceramic base member is not limited to that shown in FIGS. 2 to 4, and various configurations may be selectively employed. For example, the shape of the ceramic base member is not limited to a columnar shape, and an arbitrary shape may be employed. For example, a flat plate shape may be employed. Further, the material of the ceramic base member is not limited to alumina, and various kinds of ceramic materials may be selectively employed. For example, mullite or spinel may be employed.

In the respective embodiments, various configurations may be selectively employed for the electrode pad. For example, the shape of the first layer 121a is not limited to a rectangle, and an arbitrary shape such as an ellipse or a polygon may be employed. Each of the second layers 121b, 121c may also assume an arbitrary shape. Further, the first layer and the second layer may have a thickness different from the values explained with reference to FIG. 7, respectively. Furthermore, the first layer may be made thinner than the second layer.

The main component of the first layer of the electrode pad is not limited to tungsten, and various conductive materials such as molybdenum may be selectively employed. Like the first layer, various conductive materials may also be selectively employed as the main component of the second layer.

In the respective embodiments, the configuration of the coupling terminal is not limited to that shown in FIGS. 5 to 8 or the configuration shown in FIGS. 9 to 13, and various configurations may be selectively employed. For example, a round rod may be employed in place of the flat plate in the case of forming the members 133, 134 (FIGS. 5, 6) and the members 133a, 134a (FIGS. 9, 10). Further, in the embodiment shown in FIG. 6, the step-shaped bent portion may be eliminated. Further, in the embodiment shown in FIG. 10, the coupling portion 134a may be bent in a step shape in the thickness direction. Further, the crimping portions 135, 135a may be eliminated. Furthermore, the coupling terminal may extend in a direction perpendicular to the surface of the ceramic base member instead of extending in a direction parallel to the surface of the ceramic base member.

The material of the coupling terminal is not limited to a nickel alloy, and various conductive materials such as copper, iron or alloys thereof may be selectively employed.

In the respective embodiments, the configuration of the joining between the coupling terminal and the electrode pad (second layer) is not limited to that shown in FIGS. 5 to 8 or the configuration shown in FIGS. 9 to 13, and various configurations may be selectively employed. For example, in the case of utilizing the coupling terminal 130 shown in FIGS. 5 and 6, the joining end portion 133 may be disposed so as to be substantially perpendicular to the electrode pad 121 (second layer 121b). Further, in FIGS. 9 to 12, the joining portion 1214a may extend to the first layer 121a over the second layer 121c.

The soldering material used for the joining is not limited to an Au—Cu alloy, and various conductive materials (for example, Cu (copper) or Ag (silver)) may be selectively employed.

In the respective embodiments, the gas sensor having a ceramic heater is not limited to the oxygen sensor shown in FIG. 1, and various kinds of gas sensors for detecting a particular gas component or measuring the concentration of a particular gas component may be selectively employed. For example, an air fuel ratio sensor or a sensor for measuring the concentration of nitrogen oxide (NOx) may be selectively employed. Furthermore, a device having the ceramic heater is not limited to a gas sensor, and various kinds of devices may be selectively employed.

It should further be apparent to those skilled in the art that various changes in form and detail of the invention as shown and described above may be made. It is intended that such changes be included within the spirit and scope of the claims appended hereto.

This application claims priority from Japanese Patent Application No. 2008-274372, which was filed on Oct. 24, 2008, and from Japanese Patent Application No. 2009-225794, which was filed on Sep. 30, 2009, the disclosures of which are incorporated herein by reference in their entirety.

What is claimed is:

1. A ceramic joining unit, comprising:
    a ceramic base member having a leading end side and a rear end side, said ceramic base member extending in a longitudinal direction;
    an electrode pad formed of at least one of tungsten and molybdenum, as a main component thereof, provided on a surface of the ceramic base member;
    a coupling terminal for electrical connection to an external circuit; and
    a joining portion which joins the electrode pad to the coupling terminal by means of a solder joint,
    wherein
    the electrode pad includes:
        a first layer in contact with the ceramic base member; and
        a second layer having an upper surface and a bottom surface, the bottom surface of the second layer being laminated on an upper surface of the first layer and in contact with the joining portion,
    wherein each of the first layer and the second layer contains a ceramic material as a main component among ceramic materials forming the ceramic base member, a content (wt %) of the ceramic material in the first layer is greater than a content (wt %) of ceramic material in the second layer, and a contour of the upper surface of the first layer is located outside of a contour of the bottom surface of the second layer at an entire periphery of the first layer.

2. The ceramic joining unit according to claim 1, wherein the first layer is thicker than the second layer.

3. The ceramic joining unit according to claim 1, wherein the joining portion is in contact with the upper surface of the first layer.

4. The ceramic joining unit according to claim 3, wherein a volume of the joining portion formed on the upper surface of the first layer is smaller than a volume of the joining portion formed on a surface of the second layer.

5. The ceramic joining unit according to claim 1, further comprising a coupling terminal having a plurality of contact surface portions in contact with the joining portion, and when viewed along a lamination direction of the electrode pad, the contour of the second layer, at an entire periphery thereof, is located outside respective contours of the contact surface portions,
  wherein a shortest distance between the contour of the second layer in a short side direction perpendicular to the longitudinal direction and the contours of the contact surface portions is equal to or larger than a maximum length of the contact surface portions in the short side direction.

6. A ceramic heater, comprising:
the ceramic joining unit as claimed in claim 1; and
a heating portion embedded in the leading end side of the ceramic base member and electrically connected to the electrode pad.

7. The ceramic heater according to claim 6,
wherein
the second layer has a center of gravity located to the rear of a center of gravity of the first layer.

8. A gas sensor, comprising:
a gas sensor element which includes:
  a solid electrolyte member configured in a cylindrical shape having a bottom portion and a closed leading end;
  an outer electrode disposed at an outer peripheral surface of the solid electrolyte member; and
  an inner electrode disposed at an inner peripheral surface of the solid electrolyte member; and
a heater which is inserted into and disposed within the gas sensor element, wherein
the heater is the ceramic heater as claimed in claim 6.

* * * * *